(12) United States Patent
Tabata et al.

(10) Patent No.: US 11,391,426 B2
(45) Date of Patent: Jul. 19, 2022

(54) LIGHT SOURCE DEVICE AND LIGHT-AMOUNT ADJUSTING METHOD

(71) Applicant: OLYMPUS CORPORATION, Tokyo (JP)

(72) Inventors: Motoki Tabata, Akishima (JP); Shuhei Hatanaka, Kobe (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 17/335,203

(22) Filed: Jun. 1, 2021

(65) Prior Publication Data

US 2021/0285609 A1    Sep. 16, 2021

Related U.S. Application Data

(63) Continuation of application No. PCT/JP2018/044470, filed on Dec. 4, 2018.

(51) Int. Cl.
*A61B 1/06* (2006.01)
*G03B 21/20* (2006.01)
(Continued)

(52) U.S. Cl.
CPC .......... *F21S 10/023* (2013.01); *A61B 1/0638* (2013.01); *A61B 1/0646* (2013.01); *F21V 7/22* (2013.01);
(Continued)

(58) Field of Classification Search
CPC ... A61B 1/0638; A61B 1/0646; A61B 1/0684; G03B 21/2013; G03B 21/2033; F21V 9/20
See application file for complete search history.

(56) References Cited

U.S. PATENT DOCUMENTS

2016/0143520 A1   5/2016   Masaki et al.

FOREIGN PATENT DOCUMENTS

| JP | 2015169691 A | 9/2015 |
| JP | 2016133746 A | 7/2016 |

(Continued)

OTHER PUBLICATIONS

International Search Report dated Feb. 26, 2019 issued in PCT/JP2018/044470.

*Primary Examiner* — Sean P Gramling
(74) *Attorney, Agent, or Firm* — Scully, Scott, Murphy & Presser, P.C.

(57) ABSTRACT

A light source device includes: light sources configured to emit kinds of light having wavelength band different from one another; dichroic mirrors that are respectively arranged on a first optical path, the dichroic mirrors having light transmission characteristics different from one another, each dichroic mirror being configured to reflect or pass light emitted from any one of the light sources; light sensors that are respectively positioned on second optical paths, each second optical path being a different optical path from the first optical path and being an optical path propagating light reflected on or passed through the dichroic mirror, each light sensor being configured to detect a light amount of light that propagates through the second optical path; and a controller configured to control a light amount ratio of the kinds of light based on the light amount respectively detected by the light sensors.

7 Claims, 15 Drawing Sheets

(51) Int. Cl.
*F21V 9/20* (2018.01)
*F21S 10/02* (2006.01)
*F21V 9/40* (2018.01)
*F21V 7/22* (2018.01)
*F21V 23/00* (2015.01)
*F21V 23/04* (2006.01)
*F21Y 115/30* (2016.01)
*F21Y 113/10* (2016.01)

(52) U.S. Cl.
CPC ................ *F21V 9/20* (2018.02); *F21V 9/40* (2018.02); *F21V 23/003* (2013.01); *F21V 23/0442* (2013.01); *G03B 21/2013* (2013.01); *G03B 21/2033* (2013.01); *F21Y 2113/10* (2016.08); *F21Y 2115/30* (2016.08)

(56) References Cited

FOREIGN PATENT DOCUMENTS

| | | | |
|---|---|---|---|
| JP | 2017099944 A | | 6/2017 |
| JP | 2018000228 A | | 1/2018 |
| KR | 20150024971 A | * | 3/2015 |
| WO | 002015016172 A1 | | 2/2015 |

* cited by examiner

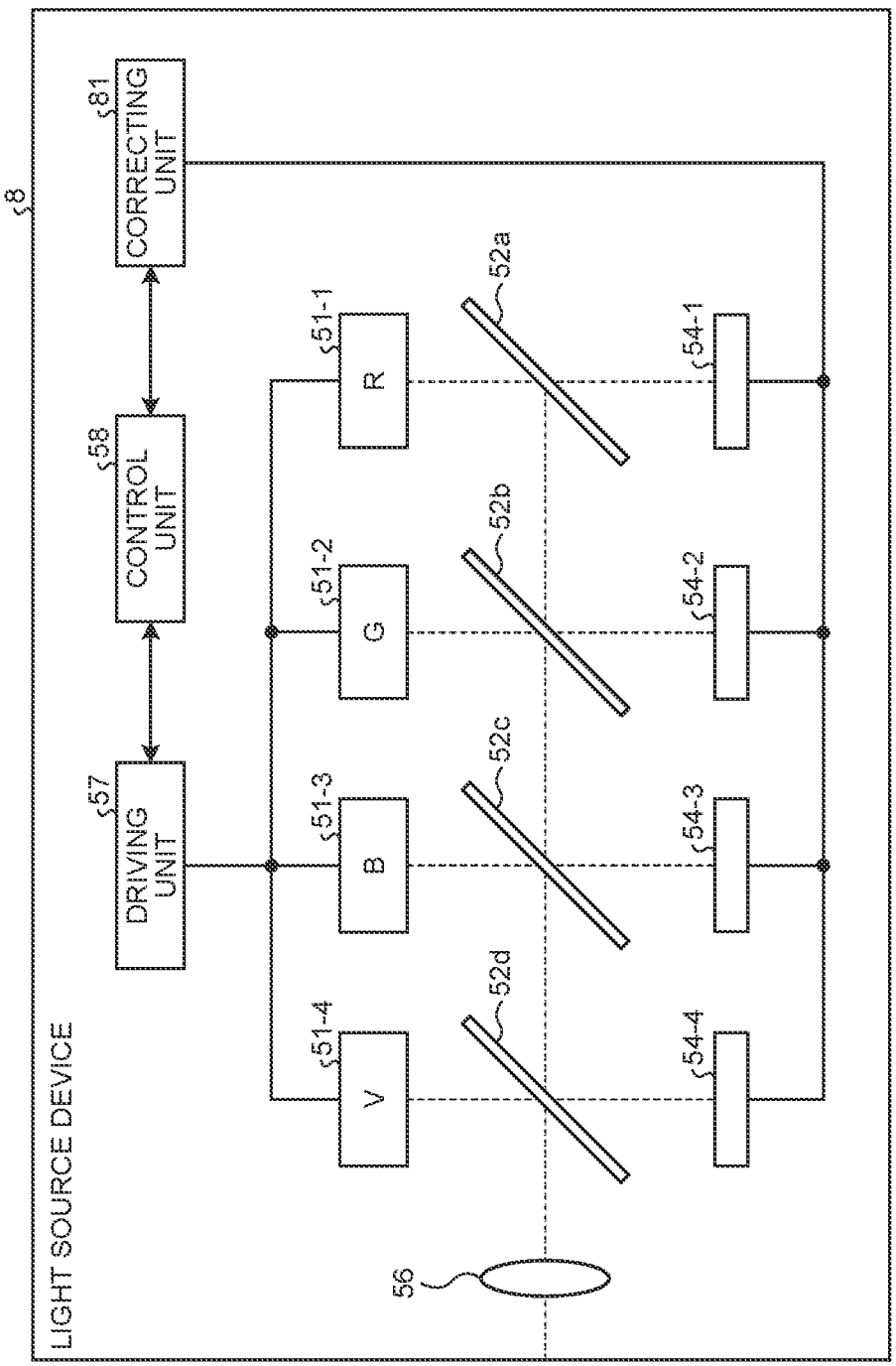

LIGHT SOURCE DEVICE AND LIGHT-AMOUNT ADJUSTING METHOD

CROSS-REFERENCE TO RELATED APPLICATION

This application is a continuation of International Application No. PCT/JP2018/044470, filed on Dec. 4, 2018, the entire contents of which are incorporated herein by reference.

BACKGROUND

1. Technical Field

The present disclosure relates to a light source device and a light-amount adjusting method.

2. Related Art

A technique of controlling output of respective light sources in a light source device including plural light sources that emit light having wavelengths different from one another by directly detecting leakage light from the light sources has been known (for example, WO2015/016172).

SUMMARY

In some embodiments, a light source device includes: a plurality of light sources configured to emit a plurality of kinds of light having wavelength band different from one another; a plurality of dichroic mirrors that are respectively arranged on a first optical path through which light is emitted to an outside, the plurality of dichroic mirrors having light transmission characteristics different from one another, each dichroic mirror being configured to reflect or pass light emitted from any one of the plurality of light sources; a plurality of light sensors that are respectively positioned on a plurality of second optical paths, each second optical path being a different optical path from the first optical path and being an optical path propagating light reflected on or passed through the dichroic mirror, each light sensor being configured to detect a light amount of light that propagates through the second optical path; and a controller configured to control a light amount ratio of the plurality of kinds of light based on the light amount respectively detected by the plurality of light sensors.

In some embodiments, a light source device includes: a first light source configured to emit light of a first wavelength band; a second light source configured to emit light of a second wavelength band; a first dichroic mirror that is arranged on a first optical path through which light is emitted to an outside of the light source device, the first dichroic mirror being configured to reflect or pass light emitted from the first light source; a second dichroic mirror that is arranged on the first optical path on a side of an emitting position of light to the outside relative to the first dichroic mirror, the second dichroic mirror having a light transmission characteristic different from the first dichroic mirror, the second dichroic mirror being configured to separate light emitted from the second light source to a component traveling to the first optical path and a component traveling to a second optical path different from the first optical path, the second dichroic mirror being configured to reflect a part of light from the first light source, which is reflected on the first dichroic mirror, toward the second optical path; and a light sensor unit that is positioned on the second optical path, the light sensor unit being configured to detect a light amount of light propagating through the second optical path. The light sensor unit includes a first light sensor to detect the light of the first wavelength band, and a second light sensor to detect the light of the second wavelength band, the first light sensor and the second light sensor are arranged at positions that are determined based on a spectral sensitivity characteristic, a maximum light amount according to a wavelength of incident light, and a light intensity distribution, the first light sensor includes at least two light sensors that are arranged at positions at which illumination intensities differ from each other in the light sensor unit, the second light sensor includes at least two light sensors that are arranged at positions at which illumination intensities differ from each other in the light sensor unit, and the light of the first wavelength band and the light of the second wavelength band are subjected to light amount detection in a dynamic range wider than a case of a single light sensor, by combining detection values of at least two light sensors.

In some embodiments, a light-amount adjusting method includes: emitting each of a plurality of kinds of light having wavelength band different from one another by a plurality of light sources; reflecting light emitted from a light source to a first optical path through which light is emitted to an outside, with a plurality of dichroic mirrors; passing the light emitted from the light source to a second optical path that is different from the first optical path, with the plurality of dichroic mirrors; detecting a light amount of light that has passed through the plurality of dichroic mirrors with a light sensor; and controlling a light amount ratio of the plurality of kinds of light based on the light amount detected by the light sensor, with a controller.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 17 is a diagram illustrating a configuration of a light source device according to a fifth embodiment.

DETAILED DESCRIPTION

Hereinafter, forms to implement the disclosure (hereinafter, "embodiment") will be explained with reference to the accompanying drawings.

First Embodiment

Figure 1:
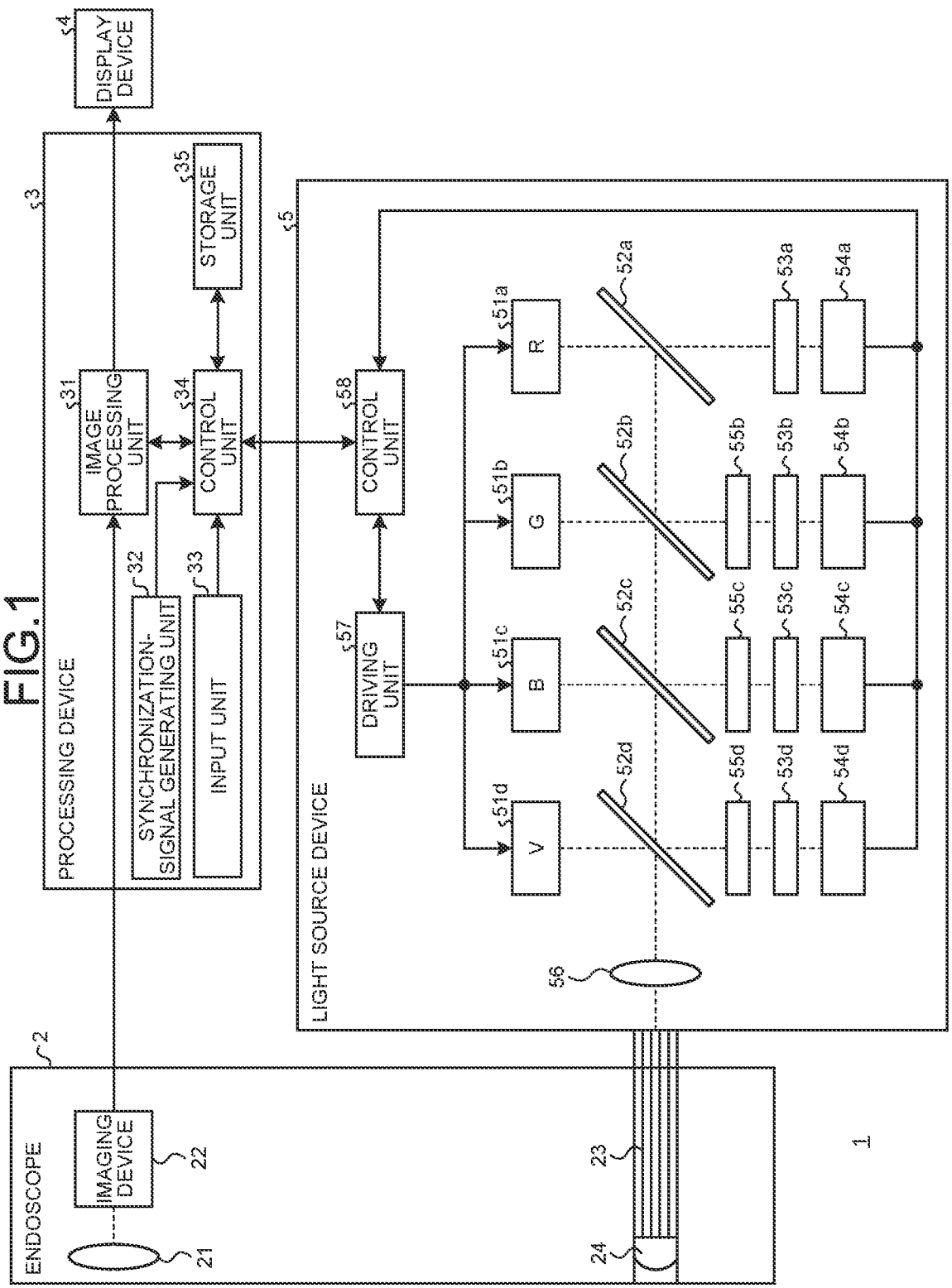
FIG. 1 is a diagram illustrating a configuration of an endoscope system that includes a light source device according to a first embodiment.

FIG. 1 is a diagram illustrating a configuration of an endoscope system that includes a light source device according to a first embodiment. An endoscope system 1 illustrated in the diagram includes an endoscope 2 that captures an in-vivo image of a subject with its distal end portion inserted into the subject, a processing device 3 that performs centralized control of an overall operation of the endoscope system 1, a display device 4 that displays an image captured by the endoscope 2, and a light source device 5 that generates illumination light emitted from a distal end of the endoscope 2.

The endoscope 2 includes an optical system 21 that is arranged at a distal end portion of an insertion portion inserted in to the subject to gather light from a subject, an imaging device 22 that generates an electrical image signal by photoelectric converting the light gathered by the optical system 21, a light guide 23 that propagates light generated by the light source device 5 to the distal end portion of the insertion portion, and an illumination lens 24 that is arranged on a distal end side of the light guide 23, and that irradiates the light that has been propagated through the light guide 23 to an outside of the endoscope 2 as illumination light. The optical system 21 is constituted of one or more lenses. The imaging device 22 is constituted of, for example, a charge coupled device (CCD) image sensor, or a complementary metal oxide semiconductor (CMOS) image sensor. The light guide 23 is constituted of, for example, plural thin optical fibers bundled.

The processing device 3 includes an image processing unit 31, a synchronization-signal generating unit 32, an input unit 33, a control unit 34, and a storage unit 35. The image processing unit 31 generates image data for display by subjecting an image signal received from the endoscope 2 to predetermined processing, and outputs it to the display device 4. The synchronization-signal generating unit 32 generates a synchronization signal to synchronize operations of the endoscope 2 and the light source device 5. The input unit 33 is constituted of a user interface, such as a switch, a button, a touch panel, a keyboard, and a mouse, and accepts an input of various kinds of signals, such as an operation instruction signal to instruct an operation of the endoscope system 1.

The control unit 34 controls the operation of the endoscope 1 including the processing device 3 in a centralized manner. The control unit 34 is configured by using hardware including a general-purpose processor, such as a central processing unit (CPU), and a dedicated integrated circuit that performs a specific function, such as a field programmable gate array (FPGA), alone or in combination.

The storage unit 35 stores various kinds of programs to operate the endoscope system 1, and data including various kinds of parameters necessary for the operation of the endoscope system 1. It is constituted of a volatile memory, such as a random access memory (RAM), and a non-volatile memory, such as a read only memory (ROM). The storage unit 35 may be constituted of a computer-readable recording medium, such as an externally mountable memory card. The various kinds of programs described above can be stored in a computer-readable recording medium, such as a hard disk, a flash memory, a CD-ROM, a DVD-ROM, and a flexible disk, to be widely distributed.

The display device 4 displays a display image corresponding to the image data received from the image processing unit 31 of the processing device 3. The display device 4 is constituted of a monitor, such as a liquid crystal or an organic electroluminescence (EL) monitor.

The light source device 5 includes four light source units 51a to 51d that generate laser light having wavelength different from one another. The light source unit 51a has a red semiconductor laser, the light source unit 51b has a green semiconductor laser, the light source unit 51c has a blue semiconductor laser, and the light source unit 51d has a violet semiconductor laser. The semiconductor laser is also called laser diode (LD).

On an optical path of red laser light generated by the light source unit 51a, a dichroic mirror 52a is arranged. A surface of the dichroic mirror 52a is slanted by 45° to an incident optical path of the red laser light, and on this surface, the red laser light is reflected to change a direction of its optical path by 90°. Hereinafter, an optical path of the red laser light after reflection on the dichroic mirror 52a is referred to as first optical path.

Figure 2:
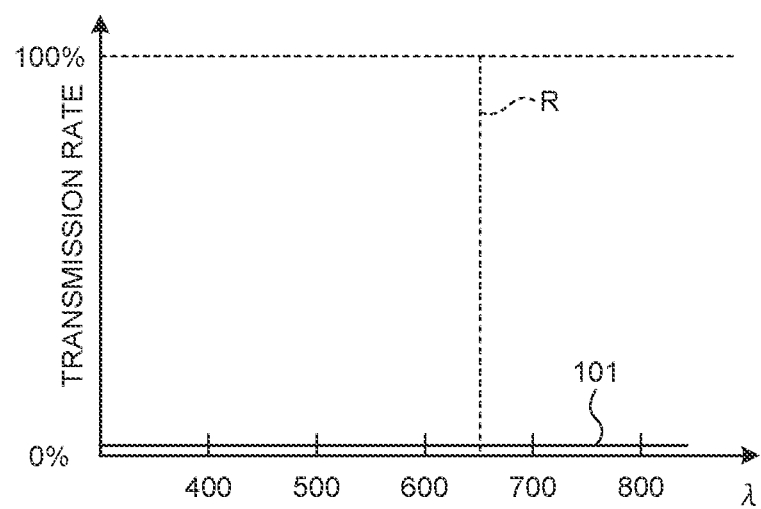
FIG. 2 is a diagram illustrating transmission characteristics of dichroic mirror that reflects red laser light.

FIG. 2 is a diagram illustrating transmission characteristics of the dichroic mirror 52a. In FIG. 2, a horizontal axis is for a wavelength and a vertical axis is for a transmission rate, and bars in broken lines R, G, B, V show center wavelengths of red, green, blue, and violet, respectively. These points are same in FIG. 3 to FIG. 8 described later.

The dichroic mirror 52a does not pass almost all wavelength bands as indicated by a straight line 101 in FIG. 2. Accordingly, the dichroic mirror 52a reflects most, and passes a very small amount of red laser light entering from the light source unit 51a. Hereinafter, an optical path of the red laser light that has passed through the dichroic mirror 52a is referred to as second optical path. On the second optical path, a neutral density (ND) filter 53a and a light sensor 54a are sequentially arranged toward downstream. The light sensor 54a only receives red laser light.

On an optical path of green laser light generated by the light source unit 51b, a dichroic mirror 52b is arranged. A surface of the dichroic mirror 52b is slanted by 45° to an incident optical path of the green laser light, and on this surface, the green laser light is reflected to change a direction of its optical path by 90°. The surface of the dichroic mirror 52b is parallel to the surface of the dichroic mirror 52a, and a reflection optical path of green laser light coincides with the first optical path. On an optical path after transmission of the green laser light through the dichroic mirror 52b (this is also referred to as second optical path), an optical filter 55b, an ND filter 53b, and a light sensor 54b are sequentially arranged toward downstream of the second optical path.

Figure 3:
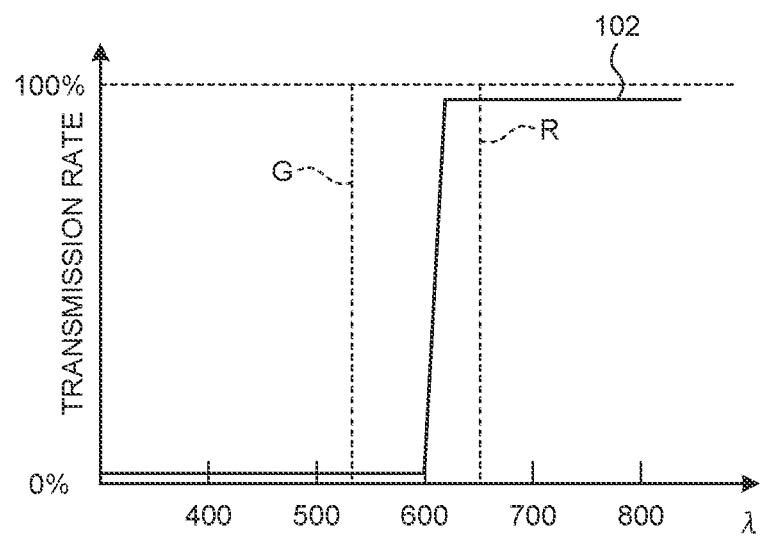
FIG. 3 is a diagram illustrating transmission characteristics of a dichroic mirror that reflects green laser light.

FIG. 3 is a diagram illustrating transmission characteristics of the dichroic mirror 52b. The dichroic mirror 52b passes most of red laser light out of four colors of laser light as indicated by a curve 102 in FIG. 3, and passes little laser light of the other three colors. Accordingly, while passing most of red laser light propagated through the first optical path, the dichroic mirror 52b reflects most of green laser light entering from the light source unit 51b, and multiplexes these kinds of laser light to let it propagate through the first optical path. Moreover, the dichroic mirror 52b reflects a very small amount of red laser light, and passes a very small amount of green laser light, to let it propagate through the second optical path.

Figure 4:
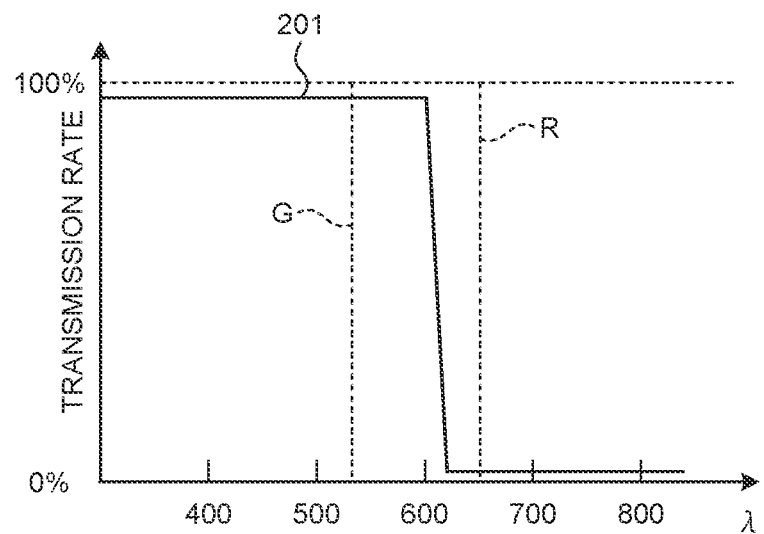
FIG. 4 is a diagram illustrating transmission characteristics of an optical filter that passes only light of a wavelength band shorter than red light.

FIG. 4 is a diagram illustrating transmission characteristics of the optical filter 55b. While passing most of light having a wavelength shorter than red as indicated by a curve 201 in FIG. 4, the optical filter 55b passes little light of a wavelength band on a longer wavelength side from the wavelength band. Therefore, the optical filter 55b passes only green laser light out of laser light that propagates through the second optical path. As a result, the light sensor 54b receives only green laser light.

On an optical path of blue laser light generated by the light source unit 51c, a dichroic mirror 52c is arranged. A surface of the dichroic mirror 52c is slanted by 45° to an incident optical path of the blue laser light, and on this surface, the blue laser light is reflected to change a direction of its optical path by 90°. The surface of the dichroic mirror 52c is parallel to the surface of the dichroic mirror 52a, and a reflection optical path of blue laser light coincides with the first optical path. On an optical path after transmission of the blue laser light through the dichroic mirror 52c (this is also referred to as second optical path), an optical filter 55c, an ND filter 53c, and a light sensor 54c are sequentially arranged toward downstream of the second optical path.

Figure 5:
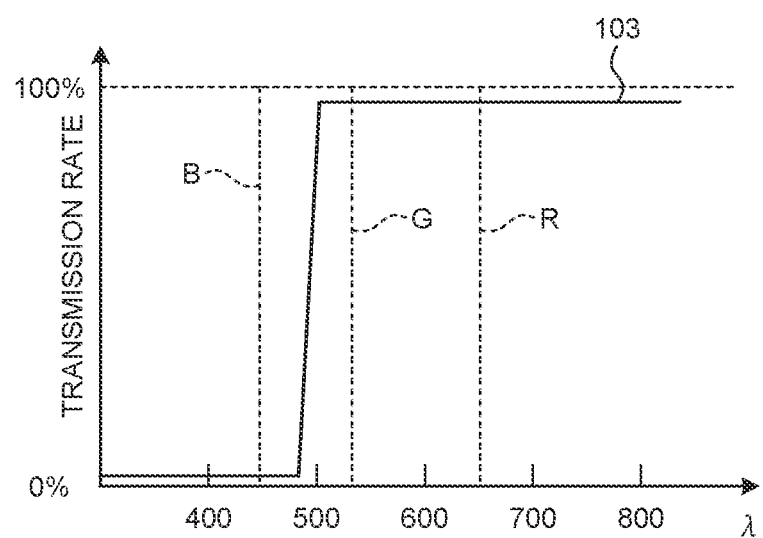
FIG. 5 is a diagram illustrating transmission characteristics of a dichroic mirror that reflects blue laser light.

FIG. 5 is a diagram illustrating transmission characteristics of the dichroic mirror 52c. As indicated by a curve 103 in FIG. 5, the dichroic mirror 52c passes most of red laser light and green laser light out of laser light of four colors, and passes little blue laser light and little violet laser light. Accordingly, while passing most of red laser light and green laser light that have propagated through the first optical path, the dichroic mirror 52c reflects most of blue laser light entering from the light source unit 51c, and multiplexes these kinds of laser light to let them propagate through the first optical path. Moreover, the dichroic mirror 52c reflects a very small amount of red laser light and green laser light, and passes a very little amount of blue laser light to let it propagate through the second optical path.

Figure 6:
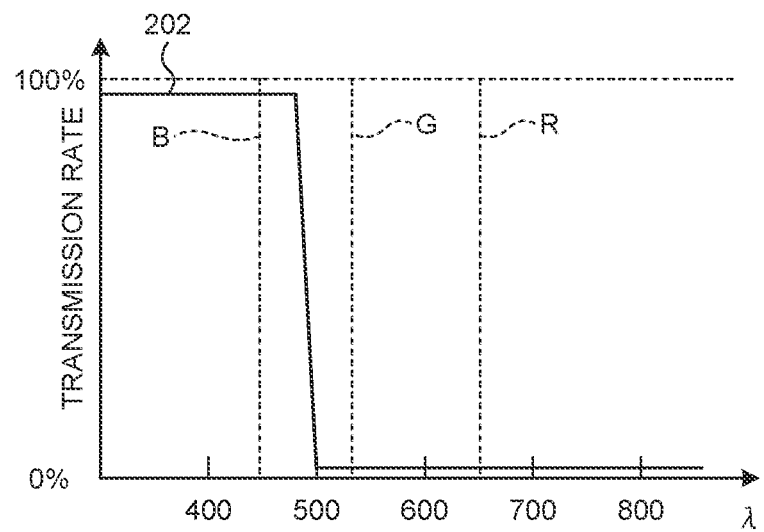
FIG. 6 is a diagram illustrating transmission characteristics of an optical filter that passes only light of a wavelength band shorter than green light.

FIG. 6 is a diagram illustrating transmission characteristics of an optical filter 55c. As indicated by a curve 202 in FIG. 6, the optical filter 55c passes most of light of a wavelength band shorter than green, and passes little light of a wavelength band on a long wavelength side from the wavelength band. Therefore, the optical filter 55c passes only blue laser light out of laser light that propagates through the second optical path. As a result, the light sensor 54c receives only blue laser light.

On an optical path of violet laser light generated by the light source device 51d, a dichroic mirror 52d is arranged. A surface of the dichroic mirror 52d is slanted by 45° to an incident optical path of the violet laser light, and on this surface, the violet laser light is reflected to change a direction of its optical path by 90°. The surface of the dichroic mirror 52d is parallel to the surface of the dichroic mirror 52a, and a reflection optical path of violet laser light coincides with the first optical path. On an optical path after transmission of the violet laser light through the dichroic mirror 52d (this is also referred to as second optical path), an optical filter 55d, an ND filter 53d, and a light sensor 54d are sequentially arranged toward downstream of the second optical path.

Figure 7:
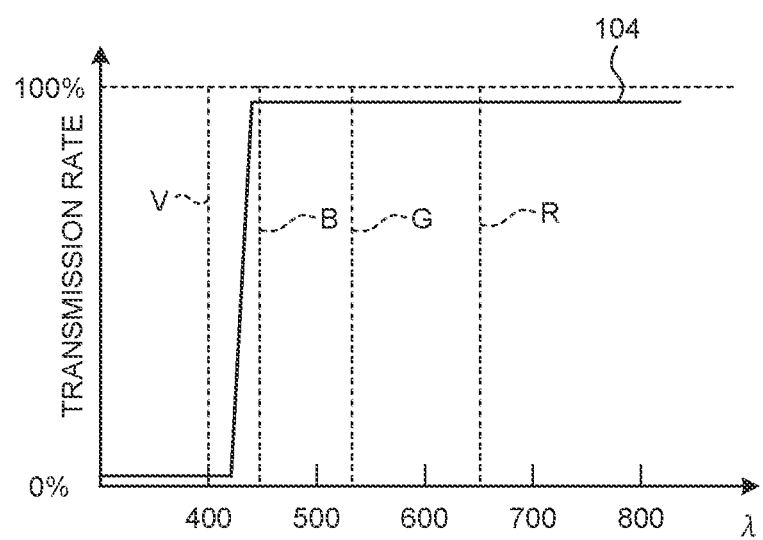
FIG. 7 is a diagram illustrating transmission characteristics of a dichroic mirror that reflects violet laser light.

FIG. 7 is a diagram illustrating transmission characteristics of the dichroic mirror 52d. As indicated by a curve 104 in FIG. 7, the dichroic mirror 52d passes laser light of three colors except violet laser light, out of laser light of four colors. Accordingly, while the dichroic mirror 52d passes most of red laser light, green laser light, and blue laser light that have propagated through the first optical path, the dichroic mirror 52d reflects most of violet laser light entering from the light source unit 51d, and multiplexes these kinds of light to let them propagate through the first optical path. Moreover, the dichroic mirror 52d reflects a very small amount of red laser light, green laser light, and blue laser light, and passes a very small amount of violet laser light to let it propagate through the second optical path.

Figure 8:
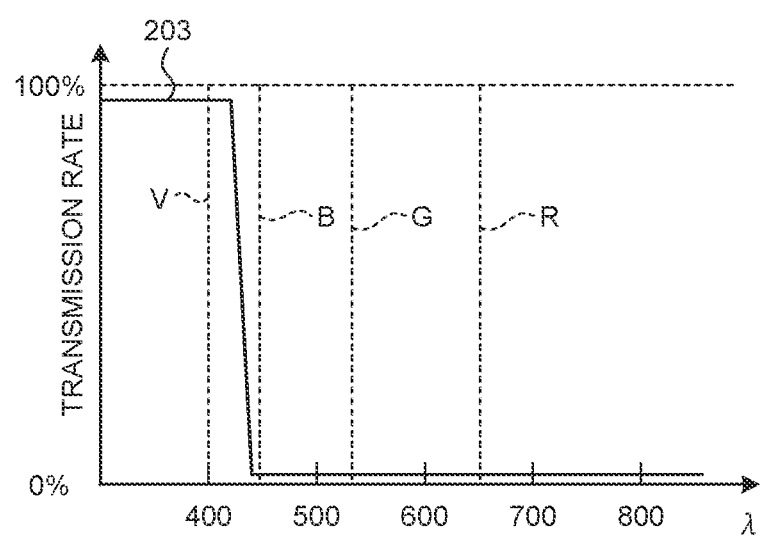
FIG. 8 is a diagram illustrating transmission characteristics of an optical filter that passes only light of a wavelength band shorter than blue light.

FIG. 8 a diagram illustrating transmission characteristics of the optical filter 55d. The optical filter 55d passes most of light of a wavelength band shorter than blue, and passes little light of a wavelength band on a long wavelength side from the wavelength band as indicated by a curve 203 in FIG. 8. Therefore, the optical filter 55d passes only violet laser light out of laser light that propagates through the second optical path. As a result, the light sensor 54d receives only violet laser light.

The ND filters 53a to 53d have a function of making a light amount of laser light of the respective colors that enters the optical sensors 54a to 54d match a light receiving range of the light sensors 54a to 54d.

The light sensors 54a to 54d are constituted of, for example, a light receiving device, such as a photodiode. Light receiving surfaces of the light sensors 54a to 54d are arranged at positions intersecting an optical path center of the second optical path perpendicularly to the optical path. Spectral sensitivity characteristics of the light sensors 54a to 54d are equal to one another.

The light source device 5 further includes a lens 56 that is arranged on the first optical path, and that gathers laser light of four colors propagating through the first optical path to supply to the light guide 23, a driving unit 57 that includes a circuit to drive the light source units 51a to 51d, and a control unit 58 that controls the driving unit 57 to drive such that a light amount ratio of plural kinds of laser beams respectively emitted from the light source units 51a to 51d is constant. The control unit 58 is constituted of a CPU, an FPGA, or the like. The light source device 5 and the processing device 3 may be integrated.

The straight line 101, the curves 102 to 104, 201 to 203 are only one example, and forms thereof are not limited to the ones illustrated.

The light source device 5 having the above configuration supplies most of light emitted respectively from the light source units 51a to 51d to the light guide 23 of the endoscope 2 through the dichroic mirrors 52a to 52d. Moreover, very small amounts out of the light emitted by the light source units 51a to 51d pass through the dichroic mirrors 52a to 52d, respectively, to propagate through the second optical path, and laser light of a single color enters the respective light sensors 54a to 54d.

The control unit 58 controls an output of the light source units 51a to 51d by driving the driving unit 57 such that respective color components of illumination light emitted by the light source device 5 maintain a predetermined light amount ratio, based on light source amounts of laser light of respective colors detected by the light sensors 54a to 54d.

According to the first embodiment explained above, light sensors to detect laser light of respective colors are arranged on the second optical path that is different from the first optical path to emit illumination light to outside of the light source device 5 and, therefore, a light amount ratio of plural light sources can be maintained constant with high accuracy.

In the light amount detection disclosed in WO2015/016172 above, because direct leakage light from a light source is acquire as illumination light deviated from an optical path, it is necessary to have a configuration to deviate a part of the illumination light from the optical path on purpose, and a loss of an actual output light amount has been large. On the other hand, in the first embodiment, out of light emitted by the light source units 51a to 51d, only a small amount of light that passes through a corresponding one of the dichroic mirrors 52a to 52d is used to detect a light amount. Therefore, a light amount of each laser light can be monitored without causing an unnecessary light amount loss.

Modification

Figure 9:
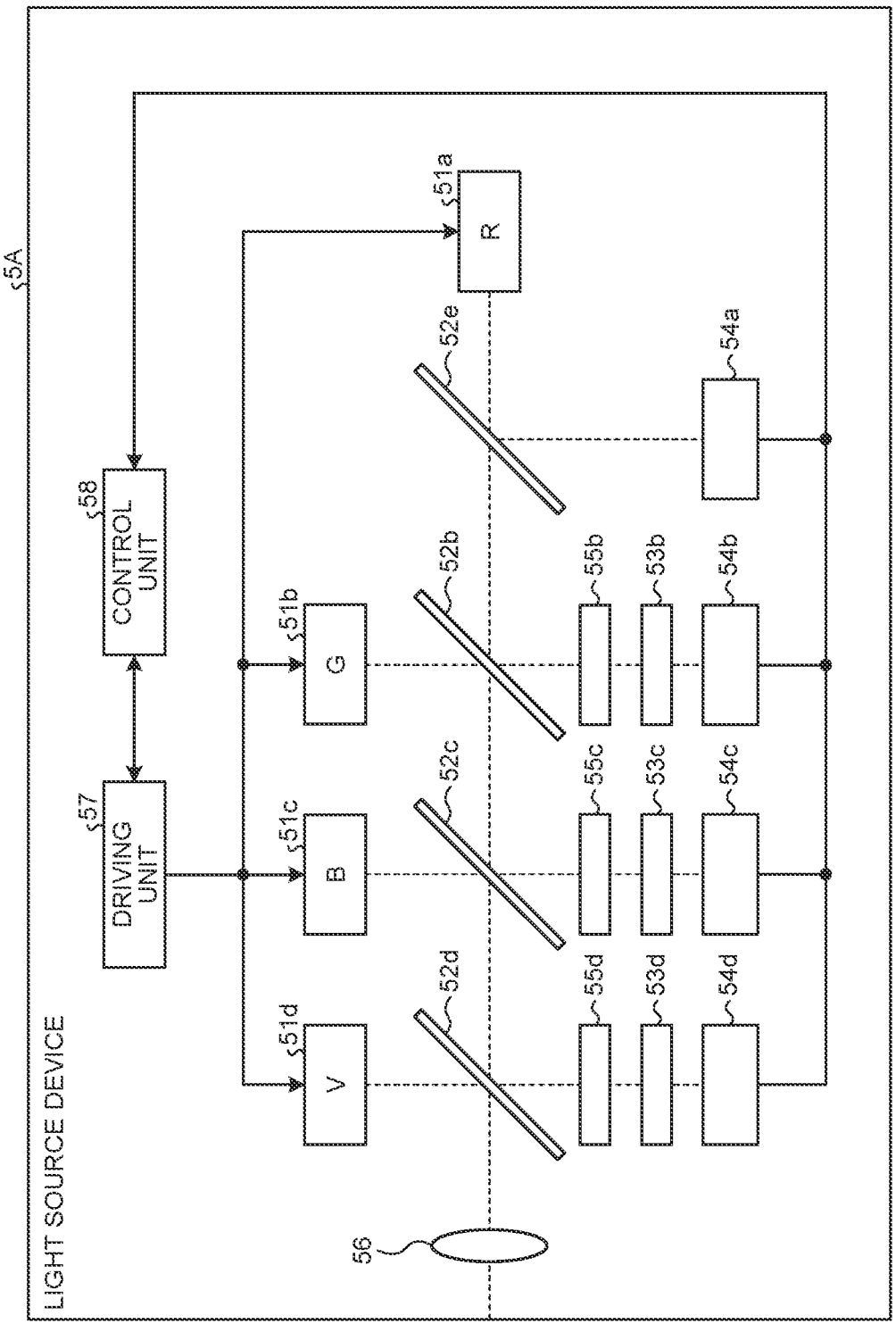
FIG. 9 is a diagram illustrating a configuration of a light source according to a modification of the first embodiment.

FIG. 9 is a diagram illustrating a configuration of a light source according to a modification of the first embodiment. In a light source device 5A illustrated in the diagram, a dichroic mirror 52e that passes most of red laser light emitted from the light source unit 51a is arranged on an incident optical path (the first optical path) of red laser light. The dichroic mirror 52e has a property that passes most of red laser light and reflects a very small amount of red laser light.

The red laser light that is reflected by the dichroic mirror 52e and propagates through the second optical path enters the light sensor 54a arranged on the second optical path. In the present modification, the ND filter 53a is not required. A configuration of the light source device 5A excluding points explained herein is the same as the configuration of the light source device 5 described above, and an acquired effect is also similar to that of the first embodiment.

Second Embodiment

A light source device according to a second embodiment sets an arrangement position of a light sensor based on a spectral sensitivity of the light sensor. Configurations of the light source device and an endoscope system excluding this point are same as those of the first embodiment. Hereinafter, explanation will be given, assigning reference symbols identical to the components of the light source device 5 to components identical to the components of the light source device 5.

Figure 10:
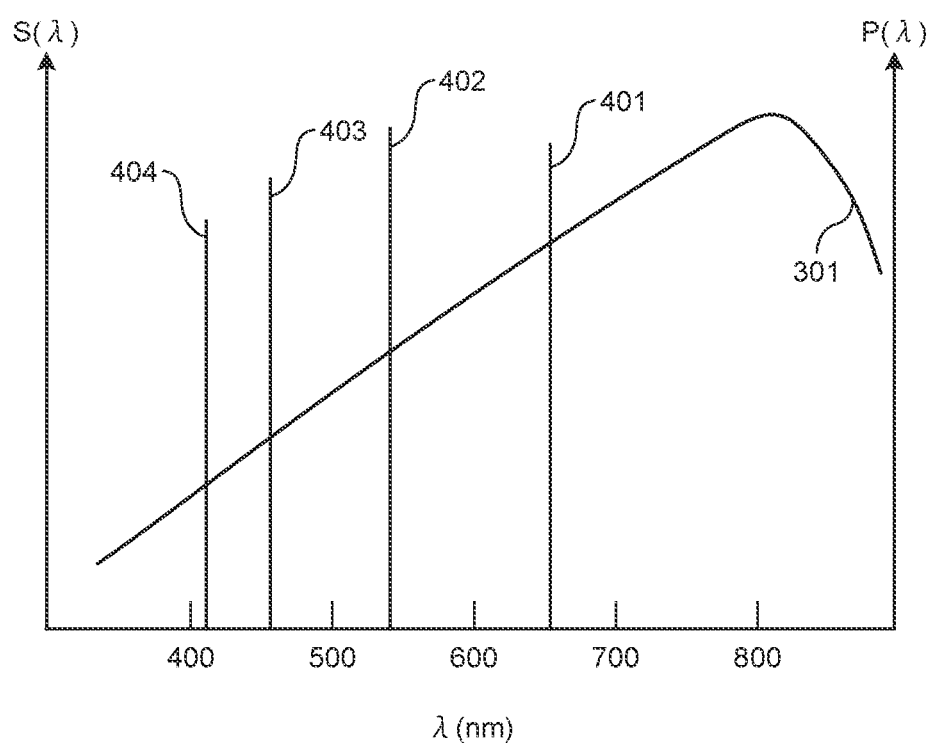
FIG. 10 is a diagram illustrating a relation between a wavelength of light and a spectral sensitivity of a light sensor, and a relation between a wavelength of incident laser light of respective colors and a maximum light amount entering a light sensor.

FIG. 10 is a diagram illustrating a relation between a wavelength λ of light and a spectral sensitivity S(λ) of a light sensor, and a relation between a wavelength λ of incident laser light of respective colors and a maximum light amount P(λ) entering a light sensor. In FIG. 10, a curve 301 is a curve indicating a spectral sensitivity S(λ). Moreover, heights of bars 401, 402, 403, 404 indicate maximum light amount P(λ) of red laser light, green, laser light, blue laser light, and violet laser light, respectively.

In the case shown in FIG. 10, the spectral sensitivity S(λ) monotonously increases with the increase of wavelength to reach the maximum value near 80 nm in a wavelength band of about 400 nm to 800 nm, and monotonously decreases with the increase of wavelength in a wavelength band higher than that. Moreover, in the case shown in FIG. 10, the maximum light mounts P(λ) entering the light sensor is green, red, blue, and violet sequentially in descending order. The curve 301 is only one example, and the spectral characteristic of the light sensor is not limited thereto.

An intensity distribution of laser light that is emitted by a semiconductor laser constituting the light source units 51a to 51d is expressed by a Gaussian distribution in which a center is the maximum value when a distance from the center of laser light is a function. In the second embodiment, as the intensity distribution of laser light, a relative light intensity I(r) at a position r when a center of the second optical path is zero in the light receiving surface is applied.

Figure 11:
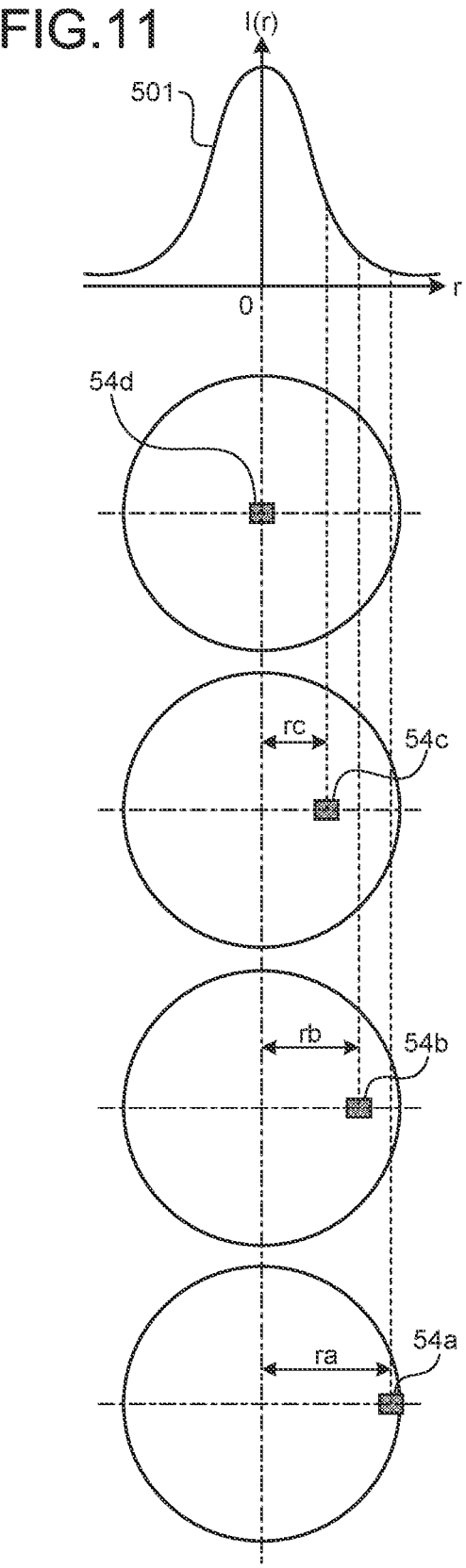
FIG. 11 is a diagram schematically illustrating an arrangement position of a light sensor included in a light source device according to a second embodiment.

FIG. 11 is a diagram schematically illustrating arrangement positions of the light sensors 54a to 54d. In FIG. 11, a curve 501 is a curve indicating a relative light intensity I(r) according to a position r. Arrangement positions of the light sensors 54a to 54d in FIG. 11 are arrangement position when it is viewed on a plane perpendicular to the second optical path. Diameters of four circles correspond to beam diameters of laser light. The beam diameter is a distance between two positions at which the relative light intensity is $I/e^2$ when the maximum value of the relative light intensity I (λ) is 1. The light sensors 54a to 54d are arranged at positions at which a product of the maximum incident light amount P(λ), the relative light intensity I(r) at the position r, and the spectral sensitivity S(λ), P(λ)×I(r)×S(λ) is uniform with one another.

In the light sensors 54a to 54d, when distances |r| from the optical path center to the positions at which the product P(λ)×I(r)×S(λ) is constant are ra, rb, rc, and rd, respectively, these distances have a relation of ra>rb>rc>rd=0 as illustrated in FIG. 11. By thus arranging the light source units 51a to 51d, it is possible to irradiate laser light of illumination intensity equivalent to one another to the light sensors 54a to 54d when the outputs of the light source units 51a to 51d are maximized.

According to the second embodiment explained above, a light amount ratio of plural light sources can be maintained constant with high accuracy similarly to the first embodiment.

Moreover, according to the second embodiment, by adjusting arrangement positions of respective light sensors on an optical path, incident light amounts to respective light sensors can be optimized.

Furthermore, according to the second embodiment, it is possible to increase a dynamic range of a light sensor without using an ND filter. When the dynamic range of a light sensor is increased by using an ND filter, it is necessary to adjust an optical concentration of the respective ND filters to be optimized, considering a spectral sensitivity characteristic and a light amount ratio. On the other hand, according to the second embodiment, because an ND filter is not necessary, it is possible to reduce the number of parts, and is not necessary to optimize ND filters independently. Consequently, it is possible to prevent similar parts from being mistaken in combination at the time of assembling a product, and to simplify an assembly procedure. Therefore, it is possible to suppress cost necessary for manufacturing, and to provide an economical light source device.

Third Embodiment

Figure 12:
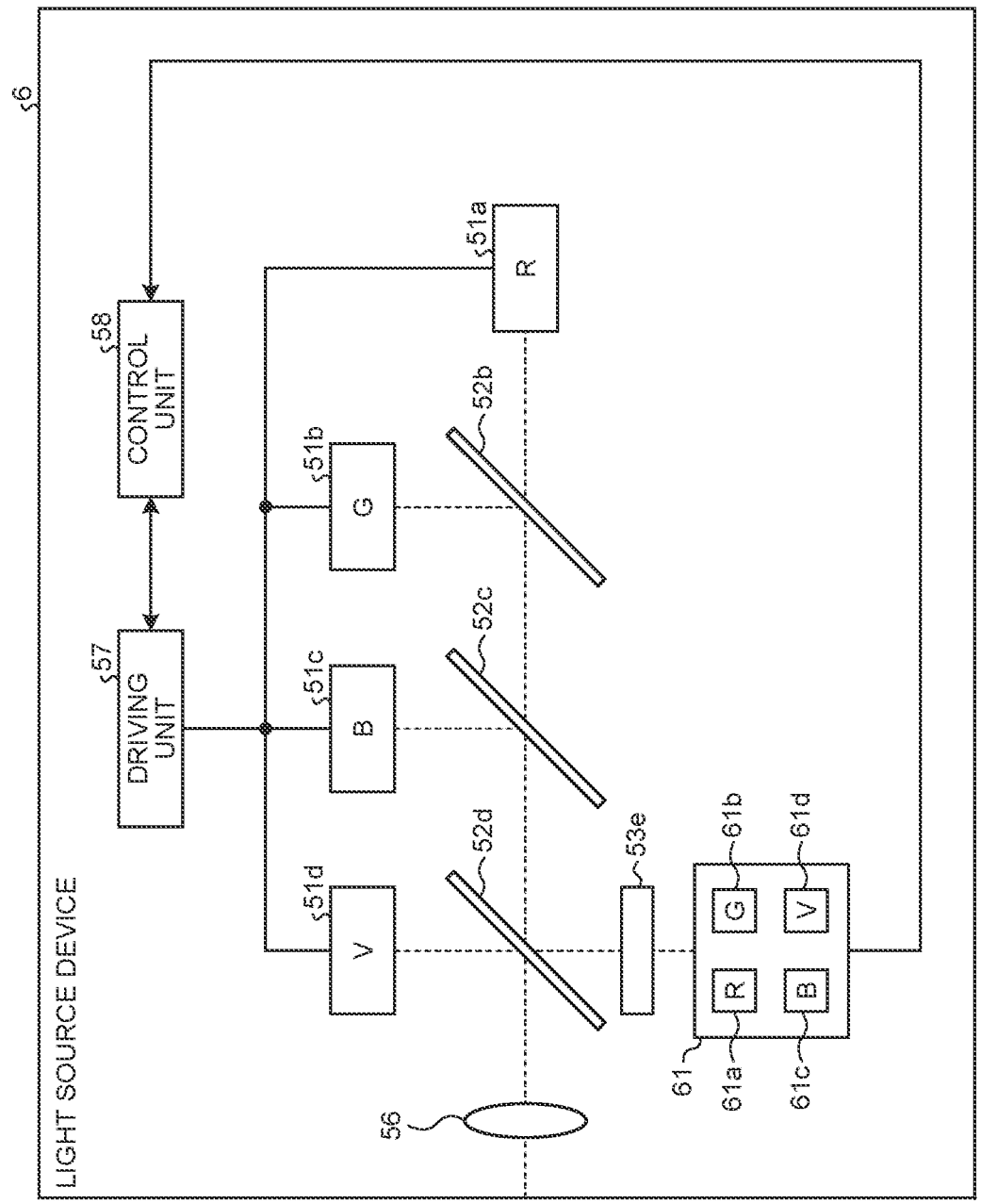
FIG. 12 is a diagram illustrating a configuration of a light source device according to a third embodiment.

FIG. 12 is a diagram illustrating a configuration of a light source device according to a third embodiment. A light source device 6 illustrated in the diagram includes the four light source units 51a to 51d, the three dichroic mirrors 52b to 52d, an ND filter 53e, the driving unit 57, the control unit 58, and a light sensor unit 61. Hereinafter, explanation will be given, assigning reference symbols identical to the components of the light source device 5 to components identical to the components of the light source device 5.

The light sensor unit 61 includes four light sensors 61a to 61d that detect red laser light, green laser light, blue laser light, and violet laser light, respectively. Each of the light sensors 61a to 61d is structured by combining an optical filter that passes a wavelength band different from others, and an optical device, such as a photodiode. FIG. 13A to FIG. 13D are diagrams showing transmission characteristics of the optical filters of the respective light sensors 61a to 61d. In FIG. 13A to FIG. 13D, a horizontal axis is for a wavelength and a vertical axis is for a transmission rate, and bars R, G, B, V in broken lines indicate center wavelengths of red, green, blue, and violet, respectively.

Figure 13A:
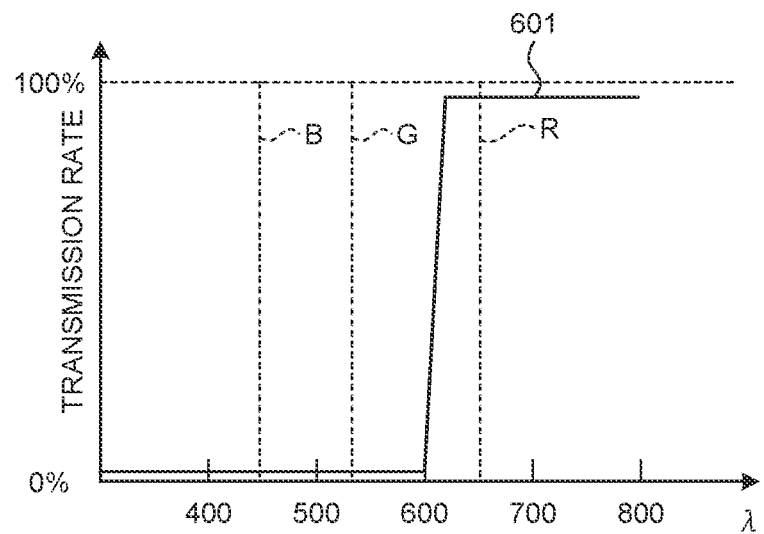
FIG. 13A is a diagram illustrating transmission characteristics of an optical filter that passes only light of a wavelength longer than a wavelength band of red light.

The optical filter included in the light sensor 61a passes most of light of red and in a wavelength band on a long wavelength side from red, and passes little light of green, blue, and violet as indicated by a curve 601 in FIG. 13A. Thus, the light sensor 61a detects a light amount of only red laser light out of laser light of four colors reflected on the dichroic mirror 52d.

Figure 13B:
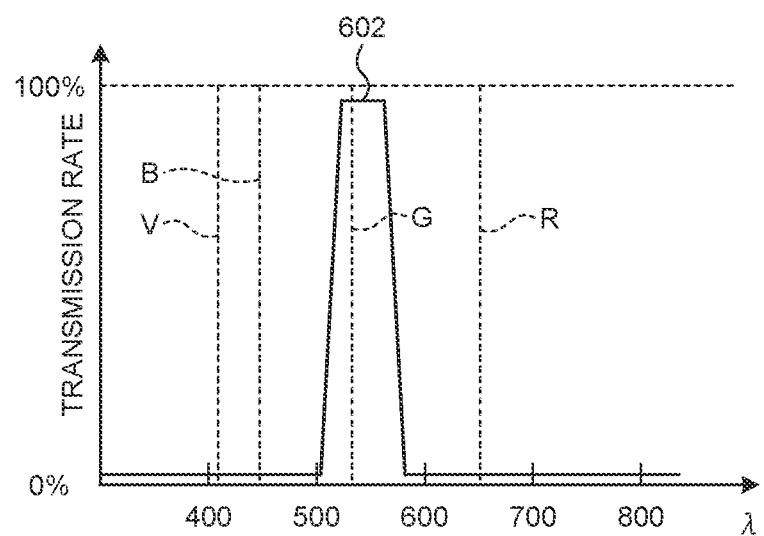
FIG. 13B is a diagram illustrating transmission characteristics of an optical filter that passes only light of a wavelength band near green light.

The optical filter included in the light sensor 61b passes most of light in a wavelength band near green, and passes little light of red, blue, and violet as indicated by a curve 602 in FIG. 13B. Thus, the light sensor 61b detects a light amount of only green laser light out of laser light of four colors reflected on the dichroic mirror 52d.

Figure 13C:
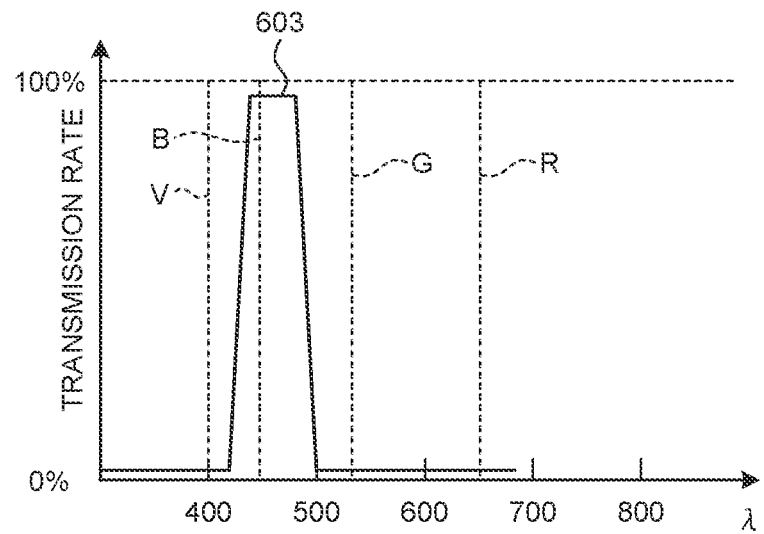
FIG. 13C is a diagram illustrating transmission characteristics of an optical filter that passes only light of a wavelength band near blue light.

The optical filter included in the light sensor 61c passes most of light in a wavelength band near blue, and passes little light red, green, and violet as indicated by a curve 603 in FIG. 13C. Thus, the light sensor 61c detects a light amount of only blue laser light out of laser light of four colors reflected on the dichroic mirror 52d.

Figure 13D:
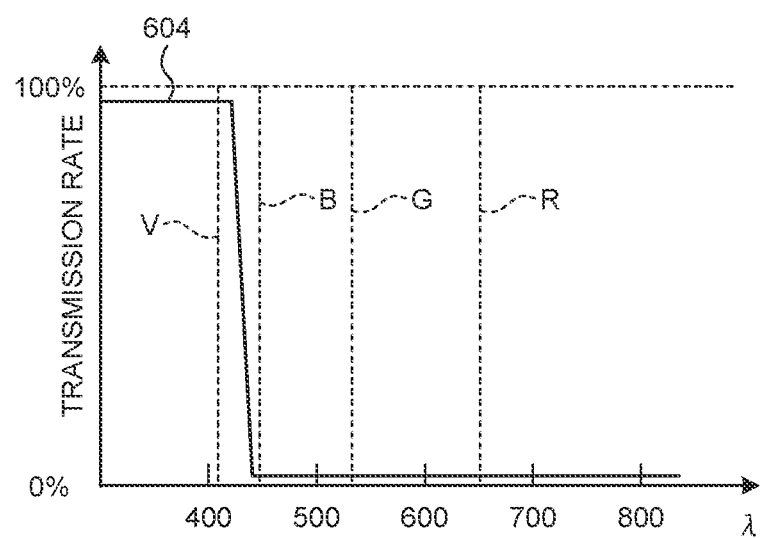
FIG. 13D is a diagram illustrating transmission characteristics of an optical filter that passes only light of a wavelength shorter than a wavelength band near violet light.

The optical filter included in the light sensor 61d passes most of light of violet and in a wavelength band on a short wavelength side from violet, and passes little light of red, green, and blue as indicated by a curve 604 in FIG. 13D. Thus, the light sensor 61d detects a light amount of only violet laser light out of laser light of four colors reflected on the dichroic mirror 52d.

The curves 601 to 604 are only one example, and forms thereof are not limited to the ones illustrated.

In the third embodiment, the light sensors 61a to 61d apply the relative light intensity I(r) at the position r when the center of the second optical path is zero in the light receiving surface as the intensity distribution of laser light similarly to the second embodiment, and the light sensors 61a to 61d are arranged at positions at which a product of the maximum incident light amount P(λ), the relative light intensity I(r) at the position r, and the spectral sensitivity S(λ), P(λ)×I(r)×S(λ) is uniform with one another.

Figure 14:
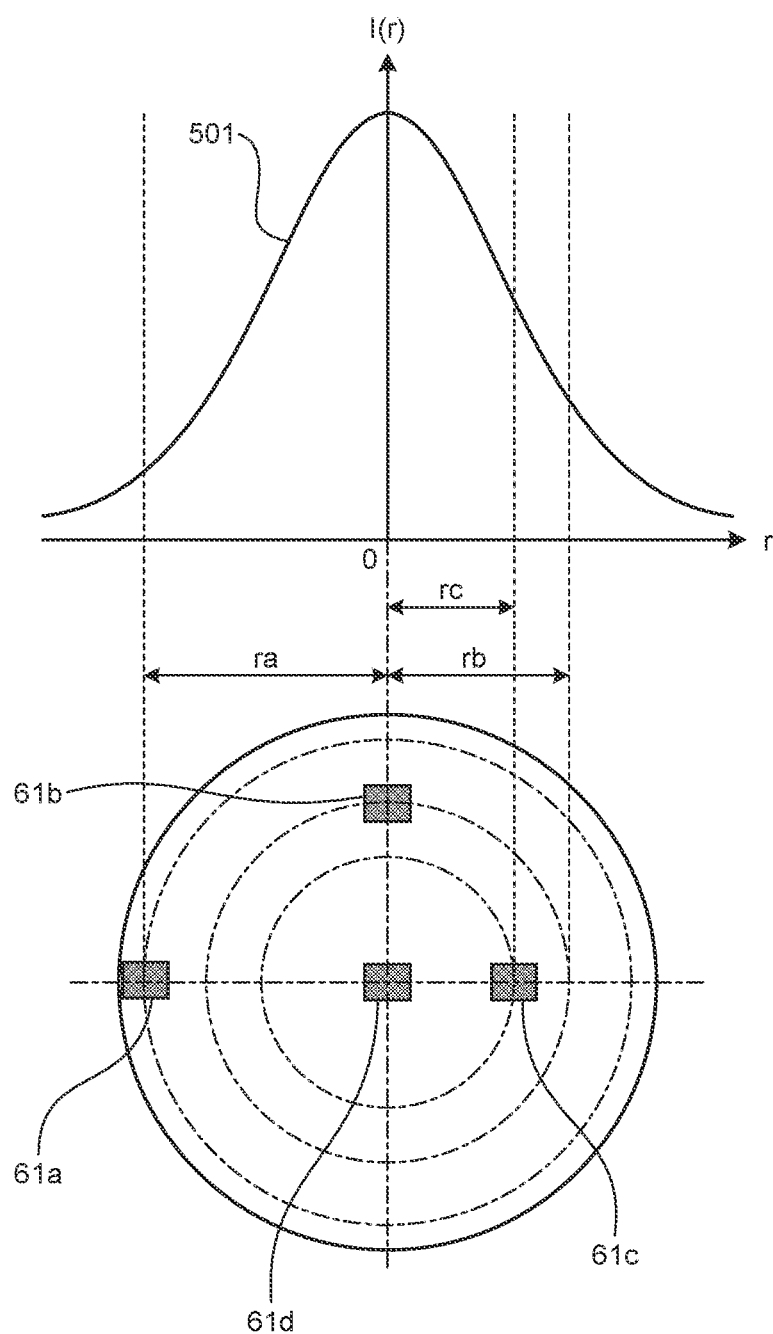
FIG. 14 is a diagram schematically illustrating an arrangement position of a light sensor included in a light source device according to a third embodiment.

FIG. 14 is a diagram schematically illustrating arrangement positions of light sensors 61a to 61d. Specifically, FIG. 14 schematically illustrates the arrangement positions of the light sensors 61a to 61d when the relation between the wavelength λ of light and the spectral sensitivity S(λ) of the light sensor is indicated by the curve 301 in FIG. 10, and the relation between the wavelength λ of incident laser light of each color and the maximum light amount P(λ) entering the light sensor is indicated by the bars 401 to 403 in FIG. 10. A curve 501 in FIG. 14 is a curve same as that in FIG. 11. Moreover, the arrangement positions of the light sensors 61a to 61d illustrated in FIG. 14 are the arrangement positions when it is viewed on a plane perpendicular to the second optical path, and a diameters of a circle corresponds to a beam diameter of laser light. In the case illustrated in FIG. 14 also, the distance |r| from the optical path center satisfies the relation of ra>rb>rc>rd=0 similarly to the case illustrated in FIG. 11. The arrangement positions of the light sensors 61a to 61d are only one example, and can be changed appropriately as long as the relation that P(λ)×I(r)×S(λ) is uniform is satisfied.

According to the third embodiment explained above, a light amount ratio of plural light sources can be maintained constant with high accuracy similarly to the first embodiment.

Moreover, according to the third embodiment, because the four light sensors 61a to 61d are arranged on the same second optical path in an optimized manner, it is possible to irradiate laser light of illumination intensity equivalent to one another to the light sensors 54a to 54d when the outputs of the light source units 51a to 51d are maximized.

Furthermore, according to the third embodiment, by detecting laser light of each color on the second optical path corresponding to the dichroic mirror 52d closest to an emitting position of illumination light to outside, it is possible to reduce an influence of characteristic variations or fluctuations of the dichroic mirror, and to further improve consistency with light to be supplied to the endoscope 2.

Fourth Embodiment

Figure 15:
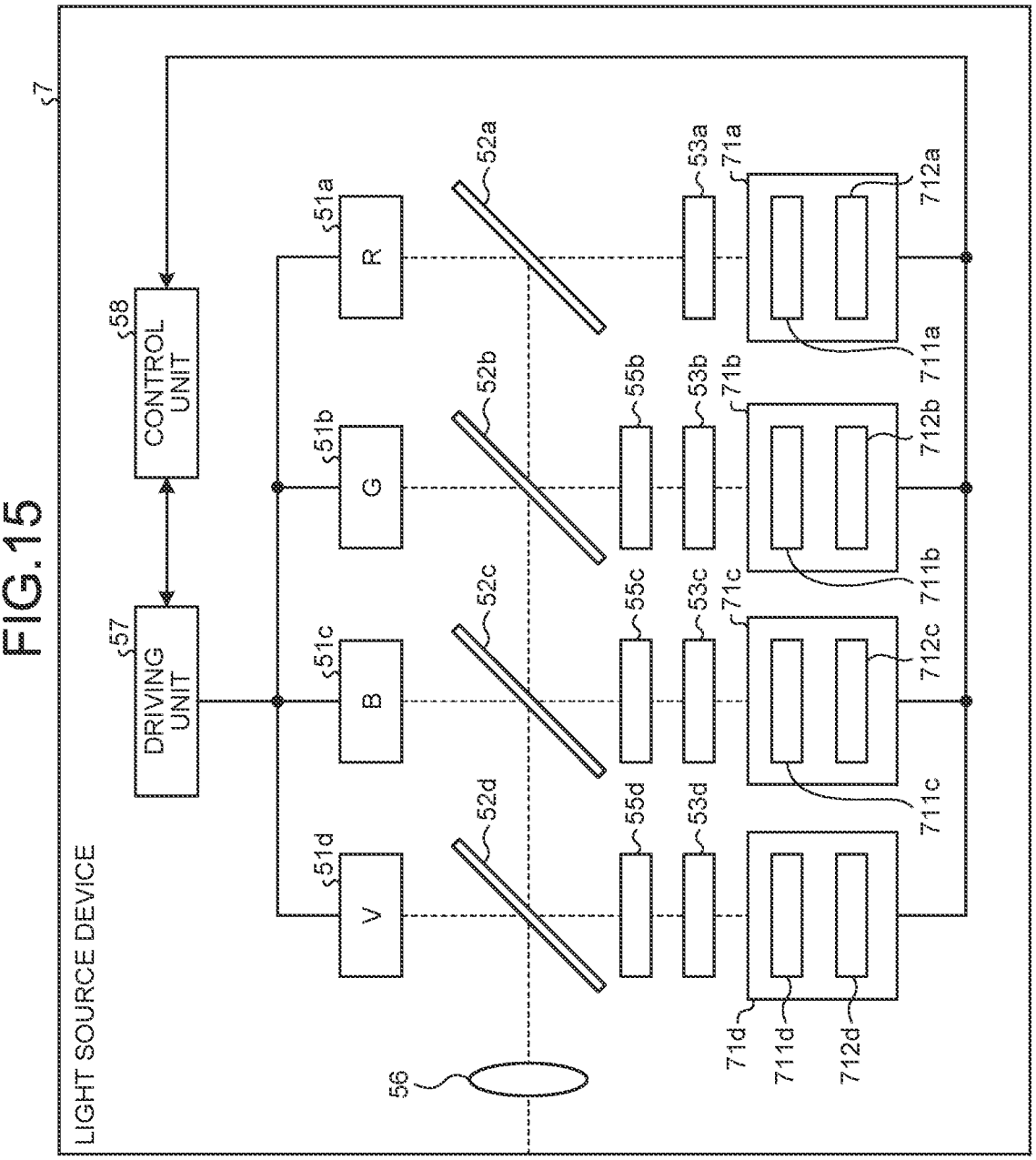
FIG. 15 is a diagram illustrating a configuration of a light source device according to a fourth embodiment.

FIG. 15 is a diagram illustrating a configuration of a light source device according to a fourth embodiment. A light source device 7 illustrated in the diagram differs in a configuration of a light sensor from the light source device 5 explained in the first embodiment. The configuration of the light source device 7 other than this point is same as the configuration of the light source device 5. Hereinafter, explanation will be given, assigning reference symbols identical to the first embodiment to components identical to the components of the light source device 5.

The light source device 7 includes four light sensor units 71a to 71d. The light sensor unit 71a includes a light sensor 711a positioned at the optical path center that is a high illumination region, and a light sensor 712a positioned in a low illumination region apart from the optical path center by about ½ of a beam diameter.

Figure 16:
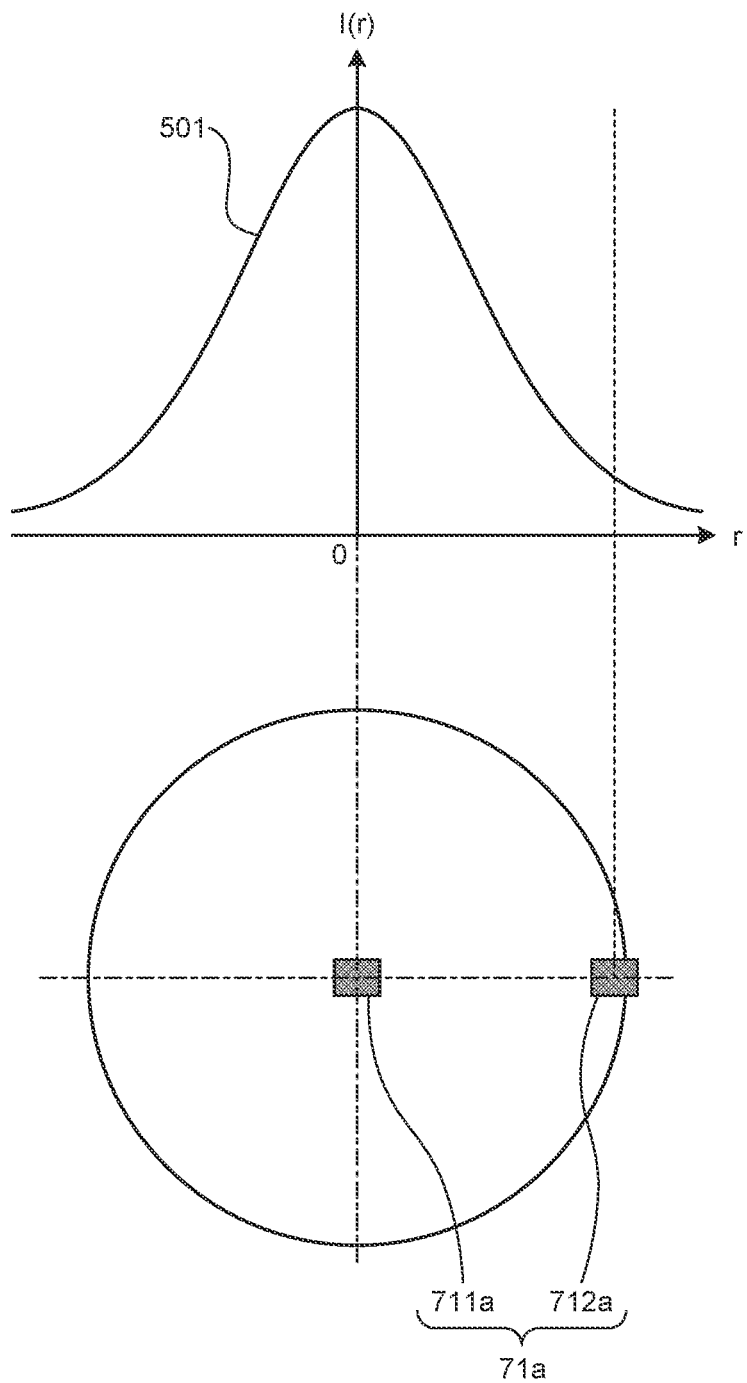
FIG. 16 is a diagram schematically illustrating an arrangement position of a light sensor included in the light source device according to the fourth embodiment.

FIG. 16 is a diagram schematically illustrating arrangement positions of the light sensors 711a and 712a in the light sensor unit 71a. The curve 501 in FIG. 16 is a curve same as that in FIG. 11. Moreover, the arrangement positions of the light sensors 711a to 712a illustrated in FIG. 16 are the arrangement positions when it is viewed on a plane perpendicular to the second optical path, and a diameters of a circle corresponds to a beam diameter.

Arrangement positions of light sensors 711b, 712b included in the light sensor unit 71b, arrangement positions of light sensors 711c, 712c included in the light sensor unit 71c, arrangement positions of light sensors 711d, 712d included in the light sensor unit 71d are also the same.

According to the fourth embodiment explained above, a light amount ratio of plural light sources can be maintained constant with high accuracy similarly to the first embodiment.

Moreover, according to the fourth embodiment, because laser light of each color is detected in a region in which an illumination intensity is different from one another for one color, it is possible to detect light of wider dynamic range compared to the case in which a single light sensor detects laser light. Therefore, it is possible to perform adjustment of light at high resolution, and it is suitable as a light source for an endoscope.

Furthermore, according to the fourth embodiment, it is possible to enlarge an illumination range just by using one set of light sensor and a common ND filter, and adjustment of a light reduction ratio of an ND filter or the like is unnecessary. Therefore, it is possible to suppress cost necessary for manufacturing, and to provide an economical light source device.

In the fourth embodiment, the number of light sensors included in each light sensor unit may be three or more.

Fifth Embodiment

FIG. 17 is a diagram illustrating a configuration of a light source device according to a fifth embodiment. A light source device 8 illustrated in the diagram does not have the ND filters 53a to 53d and the optical filters 55b to 55d unlike the light source device 5 explained in the first embodiment, but has a correcting unit 81. Hereinafter, for convenience of explanation, the light source units 51a, 51b, 51c, 51d are referred to as light source units 51-1, 51-2, 51-3, 51-4, respectively. Moreover, the light sensors 54a, 54b, 54c, 54d are referred to as light sensors 54-1, 54-2, 54-3, 54-4, respectively. To components of the light source device 8 other than these, reference symbols same as the components of the light source device 5 are assigned to be explained.

The correcting unit 81 corrects a light amount detected by the light sensors 54-1 to 54-4. The correcting unit 81 stores various kinds of programs necessary for performing a correction calculation, and various kinds of data. The correcting unit 81 is constituted of hardware, such as a CPU or an FPGA, and a memory, such as a RAM and a ROM.

Hereinafter, the correction calculation performed by the correcting unit 81 will be explained.

A detection value of the light sensor 54-$i$ ($i=1$ to 4) is $s_i$. Because the detection value $s_i$ has not passed through an optical filter, it is generally a detection value in a state in which plural kinds of light having wavelength bands different from one another are mixed in color. Out of this, a detection value $s_1$ is a detection value of only red, a detection value $s_2$ is a detection value in which red and green are mixed, a detection value $s_3$ is a detection value in which red, green and blue are mixed, and a detection value $s_4$ is a detection value in which red, green, blue, and violet are mixed.

The correcting unit 81 calculates a detection value $s'_i$ in a single color by correcting the detection value $s_i$. Specifically, a detection value $s'_1$ is a light amount of red laser light, a detection value $s'_2$ is a light amount of green laser light, a detection value $s'_3$ is a light amount of blue laser light, and a detection value $s'_4$ is a light amount of violet laser light.

The correcting unit 81 previously stores a contribution $a_{ij}$ to a light sensor 54-$j$ of laser light generated by a light source unit 51-$i$, to calculate the detection value $s'_i$. The contribution $a_{ij}$ is a detection value of the light sensor 54-$j$ when only the light source unit 51-$i$ is activated. For example, the contribution $a_{ij}$ is a detection value of the light sensor 54-1 when only the light source unit 51-1 is activated, and $a_{11}=1$. Similarly, $a_{22}=a_{33}=a_{54}=1$. Moreover, as is obvious from the configuration of the light source device 8, $a_{ij}=0$ ($i<j$). The contribution $a_{ij}$ is expresses as an element of a lower triangular matrix A below.

$$A = \begin{pmatrix} 1 & 0 & 0 & 0 \\ a_{21} & 1 & 0 & 0 \\ a_{31} & a_{32} & 1 & 0 \\ a_{41} & a_{42} & a_{43} & 1 \end{pmatrix} \quad (1)$$

As is obvious from Eq. 1, a determinant of the matrix A is 1, and has an inverse matrix $A^{-1}$. The inverse matrix $A^{-1}$ is expressed as $$A^{-1} = \begin{pmatrix} 1 & 0 & 0 & 0 \\ -a_{21} & 1 & 0 & 0 \\ -a_{31}+a_{21}a_{32} & -a_{32} & 1 & 0 \\ -a_{41}+a_{21}a_{42}+a_{31}a_{43}-a_{21}a_{32}a_{43} & -a_{42}+a_{32}a_{43} & -a_{43} & 1 \end{pmatrix} \quad (2)$$

A column vector $s=(s_1, s_2, s_3, s_4)^T$ having the detection value $s_i$ of a single color as its element, and a column vector $s'=(s'_1, s'_2, s'_3, s'_4)^T$ having the detection value $s'_i$ of mixed colors as its element are defined herein. $( \ldots )^T$ signifies a transposed matrix. At this time, the column vector s and the column vector s' have a relation of $s=As'$, or $S'=A^{-1}s$.

The correcting unit 81 corrects a light amount received by the light sensor 54-$i$ out of laser light generated by the light source unit 51-$i$ by calculating a column vector $s'=A^{-1}s$, using the column vector s having a detection value of the light sensor 54-$i$ as its element, and the matrix A for which an element $a_{ij}$ is previously stored.

According to the fifth embodiment explained above, a light amount ratio of plural light sources can be maintained constant with high accuracy similarly to the first embodiment.

Moreover, according to the fifth embodiment, because an optical filter and an ND filter are not necessary, it is possible to reduce the number of parts, to suppress cost necessary for manufacturing, and to provide an economical light source device.

Although a case in which the light source device 8 has four units each of the light source units and the light sensors has been explained, it is possible to calculate a light amount of a single color by performing a similar calculation by the correcting unit 81 also when the light source device has the same number of light source unit and light sensor more generally. For example, when the number of the light source unit and the light sensor is N (N is a positive integer), the column vectors s, s' respectively have an N element, and the matrix A having the contribution $a_{ij}$ as its element is to be a matrix of N rows and N columns, but the calculation performed by the correcting unit 81 is none other than $s'=A^{-1}s$.

Moreover, correction may be combined according to how multiplexing of light is performed in a light source device. For example, in a light source device having five units of light source units, the five light source units may be divided into a group of three units and a group of two units, to perform the correction calculation similar to the above in each group, and may synthesize light by using those.

Other Embodiments

Embodiments to implement the disclosure have so far been explained, but the disclosure is not to be limited to the first to the fifth embodiments described above. For example, the light source unit may be configured by using a light emitting diode (LED) instead of a semiconductor laser.

Furthermore, combinations of colors of plural light source units and an arrangement sequence in the first optical path are not limited to those of the embodiments described above. Transmission characteristics of plural dichroic mirrors and plural optical filters may also be adjusted according to the combinations of colors of the plural light source units and the arrangement sequence in the first optical path.

Moreover, it may be applied as a light source device of an ultrasound endoscope or an industrial endoscope, or may be applied as a light source device for purposes other than endoscopes.

According to the disclosure, a light amount ratio of plural light sources can be maintained constant with high accuracy.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source device comprising:
a first light source configured to emit light of a first wavelength band;
a second light source configured to emit light of a second wavelength band;
a first dichroic mirror that is arranged on a first optical path through which light is emitted to an outside of the light source device, the first dichroic mirror being configured to reflect or pass light emitted from the first light source;
a second dichroic mirror that is arranged on the first optical path on a side of an emitting position of light to the outside relative to the first dichroic mirror, the second dichroic mirror having a light transmission characteristic different from the first dichroic mirror, the second dichroic mirror being configured to separate the light emitted from the second light source to a component traveling to the first optical path and a component traveling to a second optical path different from the first optical path, the second dichroic mirror being configured to reflect a part of light from the first light source, which is reflected by the first dichroic mirror, toward the second optical path; and
a light sensor unit that is positioned on the second optical path, the light sensor unit being configured to detect a light amount of light propagating through the second optical path, wherein
the light sensor unit includes a first light sensor to detect the light of the first wavelength band, and a second light sensor to detect the light of the second wavelength band,
the first light sensor and the second light sensor are arranged at positions that are determined based on a spectral sensitivity characteristic, a maximum light amount according to a wavelength of incident light, and a light intensity distribution,
the first light sensor includes at least two light sensors that are arranged at positions at which illumination intensities differ from each other in the light sensor unit,
the second light sensor includes at least two light sensors that are arranged at positions at which illumination intensities differ from each other in the light sensor unit, and
the light of the first wavelength band and the light of the second wavelength band are subjected to light amount detection in a dynamic range wider than a case of a single light sensor, by combining detection values of at least two light sensors.

2. The light source device according to claim 1, wherein the light of the first wavelength band is blue light, and the light of the second wavelength band is violet light.

3. The light source device according to claim 2, wherein the first dichroic mirror is configured to reflect part of the blue light to let it propagate through the first optical path, and
the second dichroic mirror is configured to
reflect part of the violet light to let the part of the violet light propagate through the first optical path,
pass part of the blue light to let the part of the blue light propagate through the first optical path,
pass other part of the violet light to let the other part of the violet light propagate through the second optical path, and
reflect other part of the blue light to let the other part of the blue light propagate through the second optical path.

4. The light source device according to claim 3, wherein the first light sensor includes an optical filter configured to pass the violet light, and
the second light sensor includes an optical filter configured to pass the blue light.

5. The light source device according to claim 4, wherein the at least two light sensors of the first light sensor include a third light sensor positioned in a low illumination region and a fourth light sensor positioned in a high illumination region that has an illumination intensity higher than an illumination intensity of the low illumination region in which the third light sensor is positioned.

6. The light source device according to claim 5, wherein the at least two light sensors of the second light sensor include a fifth light sensor positioned in a low illumination region and a sixth light sensor positioned in a high illumination region that has an illumination intensity higher than an illumination intensity of the low illumination region in which the third light sensor is positioned, and
the fourth light sensor is positioned closer to a center of the second optical path than the sixth light sensor.

7. A method for using a light source device comprising a first light source, a second light source, a first dichroic mirror, a second dichroic mirror and a light sensor unit, the method comprising:
emitting, by the first light source, light of a first wavelength band;
emitting, by the second light source, light of a second wavelength band;
reflecting, by the first dichroic mirror that is arranged on a first optical path, the light emitted from the first light source to an outside, and passing, by the first dichroic mirror, the light emitted from the first light source;

separating, by the second dichroic mirror that is arranged on the first optical path on a side of an emitting position of light to the outside relative to the first dichroic mirror, the second dichroic mirror having a light transmission characteristic different from the first dichroic mirror, the light emitted from the second light source to a component traveling to the first optical path and a component traveling to a second optical path different from the first optical path, and reflecting, by the second dichroic mirror, a part of the light from the first light source, which is reflected by the first dichroic mirror, toward the second optical path; and detecting, by a light sensor unit that is positioned on the second optical path, a light amount of light propagating through the second optical path, wherein detecting the light amount of light propagating through the second optical path comprises:

detecting, by a first light sensor of the light sensor unit, the light of the first wavelength band; and detecting, by a second light sensor of the light sensor unit, the light of the second wavelength band, wherein the first light sensor and the second light sensor are arranged at positions that are determined based on a spectral sensitivity characteristic, a maximum light amount according to a wavelength of incident light, and a light intensity distribution, the first light sensor includes at least two light sensors that are arranged at positions at which illumination intensities differ from each other in the light sensor unit, the second light sensor includes at least two light sensors that are arranged at positions at which illumination intensities differ from each other in the light sensor unit, and the light of the first wavelength band and the light of the second wavelength band are subjected to light amount detection in a dynamic range wider than a case of a single light sensor, by combining detection values of at least two light sensors.

\* \* \* \* \*